(12) United States Patent
Ivashchenko et al.

(10) Patent No.: US 8,471,009 B2
(45) Date of Patent: Jun. 25, 2013

(54) (EN) 2-ALKYLAMINO-3-ARYLSULFONYL-CYCLOALCANO [E OR D] PYRAZOLO [1,5-A]PYRIMIDINES / ANTAGONISTS OF SEROTONIN 5-HT6 RECEPTORS, METHODS FOR THE PRODUCTION AND THE USE THEREOF

(76) Inventors: Andrey Alexandrovich Ivashchenko, Moscow (RU); Nikolay Filippovich Savchuk, Rancho Santa Fe, CA (US); Alexander Vasilievich Ivashchenko, Encinitas, CA (US)

( * ) Notice: Subject to any disclaimer, the term of this patent is extended or adjusted under 35 U.S.C. 154(b) by 319 days.

(21) Appl. No.: 12/812,734

(22) PCT Filed: Jan. 23, 2009

(86) PCT No.: PCT/IB2009/050274
§ 371 (c)(1),
(2), (4) Date: Jul. 13, 2010

(87) PCT Pub. No.: WO2009/093209
PCT Pub. Date: Jul. 30, 2009

(65) Prior Publication Data
US 2010/0292256 A1    Nov. 18, 2010

(30) Foreign Application Priority Data

Jan. 24, 2008 (RU) ................ 2008102154
May 7, 2008 (RU) ................ 2008117846
Sep. 17, 2008 (RU) ................ 2008137216

(51) Int. Cl.
*A61K 31/519* (2006.01)
*C07D 487/04* (2006.01)
(52) U.S. Cl.
USPC ......................... 544/267; 544/250
(58) Field of Classification Search
USPC ..................... 544/250; 514/267
See application file for complete search history.

(56) References Cited

FOREIGN PATENT DOCUMENTS

| EP | 0941994 | 3/1999 |
|---|---|---|
| WO | WO02/072585 | 9/2002 |
| WO | WO03/057674 | 7/2003 |

OTHER PUBLICATIONS

Ahmed, 2007, J. Heterocyclic Chem, vol. 44, p. 803-810.*
Monsma FJ Jr; Shen Y; Ward RP; Hamblin MW; Sibley DR: Cloning and expression of a novel serotonin receptor with high affinity for tricyclic psychotropic drugs. MOL PHARMACOL. vol. 43, 1993, pp. 320-327.
Woolley M.L.: 5-HT6 receptors. Curr. Drug Targets CNS Neurol. Disord. vol. 3, 2004, pp. 59-79.
Holenz J.; Pauwels P.J.; Diaz J.L.; Merce R.; Codony X.; Buschmann H.: Medicinal chemistry strategies to 5-HT6 receptor ligands as potential cognitive enhancers and antiobesity agents. Drug Disc. Today. vol. 11, 2006, pp. 283-299.
Gerard C.; Martres M.-P.; Lefevre K.; Miquel M.-C.; Verge D.; Lanfumey L.; Doucet E.; Hamon M.; El Mestikawy S.: Immunolocalisation of serotonin 5-HT6 receptor-like material in the rat central nervous system. Brain Research vol. 746, 1997, pp. 207-219.
Dawson L.A.; Nguyen H.Q.; Li P.: The 5-HT(6) receptor antagonist SB-271046 selectively enhances excitatory neurotransmission in the rat frontal cortex and hippocampus. Neuropsychopharmacology vol. 25, 2001, pp. 662-668.
Foley A.G.; Murphy K.J.; Hirst W.D.; Gallagher H.C.; Hagan J.J.; Upton N.; Walsh F.S.; Regan C.M.: The 5-HT(6) receptor antagonist SB-271046 reverses scopolamine-disrupted consolidation of a passive avoidance task and ameliorates spatial task deficits in aged rats. Neuropsychopharmacology vol. 29, 2004, pp. 93-100.

(Continued)

*Primary Examiner* — Wu-Cheng Winston Shen
*Assistant Examiner* — Karen Cheng

(57) ABSTRACT

The invention relates to substituted 2-alkylamino-3-(arylsulfonyl)cycloalkyl[e or d]pyrazolo[1,5-a]pyrimidines, to serotonin 5-HT$_6$ receptor antagonists, to novel drug substances and pharmaceutical compositions comprising the said compounds as active ingredients, and to novel medicaments and method for treatment and prophylaxis of various CNS diseases.

2-Alkylamino-3-arylsulfonylcycloalkyl[e]pyrazolo[1,5-a]pyrimidines of general formula 1 and 2-alkylamino-3-arylsulfonylcycloalkyl[d]pyrazolo[1,5-a]pyrimidines of general formula 2,

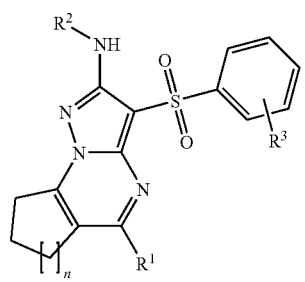

1

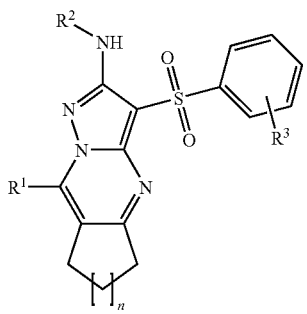

2 wherein: $R^1$ is hydrogen or $C_1$-$C_3$ alkyl; $R^2$ is $C_1$-$C_3$ alkyl; $R^3$ is hydrogen, one or more optionally identical halogen atoms, $C_1$-$C_3$ alkyl or hydroxyl group optionally substituted with $C_1$-$C_3$ alkyl; n is the whole numbers 1, 2 or 3.

10 Claims, No Drawings

OTHER PUBLICATIONS

Riemer C.; Borroni E.; Levet-Trafit B.; Martin J.R.; Poli S.; Porter R.H.; Bos M.: Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-HT6 receptor antagonist. J Med. Chem. vol. 46, 2003, pp. 1273-1276.

King M.V.; Woolley M.L.; Topham I.A.; Sleight A.J.; Marsden C.A.; Fone K.C. 5-HT6 receptor antagonists reverse delay-dependent deficits in novel object discrimination by enhancing consolidation an effect sensitive to NMDA receptor antagonism. Neuropharmacology vol. 47, 2004, pp. 195-204.

Davies S.L.: Drug discovery targets: 5-HT6 receptor. Drug Future vol. 30, 2005, pp. 479-495.

* cited by examiner

(EN) 2-ALKYLAMINO-3-ARYLSULFONYL-CYCLOALCANO [E OR D] PYRAZOLO [1,5-A]PYRIMIDINES / ANTAGONISTS OF SEROTONIN 5-HT6 RECEPTORS, METHODS FOR THE PRODUCTION AND THE USE THEREOF

CROSS REFERENCE TO RELATED APPLICATIONS

This application is a 35 U.S.C. §371 National stage of International application PCT/IB2009/050274 filed Jan. 23, 2009, which claims the benefit of foreign priority to the Russian Federation applications RU 2008102154 of Jan. 24, 2008; RU 2008117846 of May 7, 2008; RU 2008137216 of Sep. 17, 2008. The priority applications are hereby incorporated by reference in their entirety.

FIELD OF THE INVENTION

The invention relates to novel (arylsulfonyl)pyrazolo[1,5-a]pyrimidines, to novel serotonin 5-HT$_6$ receptor antagonists, drug substances, pharmaceutical compositions, medicaments, methods for their preparation and use. More specifically, the invention relates to serotonin 5-HT$_6$ receptor antagonists—substituted 2-alkylamino-3-(arylsulfonyl)-cycloalkyl[e or d]pyrazolo[1,5-a]pyrimidines, to drug substances, to pharmaceutical compositions, comprising the said compounds as active ingredients, and to methods of treatment and prophylaxis of various cognitive and neurodegenerative diseases. The origin of pharmacological effect of novel drug substances is their ability to interact with serotonin 5-HT$_6$ receptors playing the key role in treatment of central nervous system (CNS) diseases, in particular, Alzheimer's disease (AD), Huntington's disease, schizophrenia, other neurodegenerative diseases, cognitive disorders and obesity.

BACKGROUND OF THE INVENTION

Usefulness of selective antagonists of serotonin 5-HT$_6$ receptors for treating of CNS diseases, in particular, schizophrenia, AD and other neurodegenerative diseases and cognitive disorders was proved conclusively in clinical practice and is regarded to be very perspective in medicine of future [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. At mammals these receptors are localized exclusively in central nervous system (CNS), and mainly in parts of brain responsible for training and memory [Ge'rard C., Martres M.-P., Lefe'vre K., Miguel M.-C., Verge' D., Lanfumey L., Doucet E., Hamon M., El Mestikawy S. Immuno-localization of serotonin 5-HT$_6$ receptor-like material in the rat central nervous system. *Brain Research.* 1997; 746:207-219]. Besides, it was shown [Dawson L. A., Nguyen H. Q., Li P. The 5-HT(6) receptor antagonist SB-271046 selectively enhances excitatory neurotransmission in the rat frontal cortex and hippocampus. *Neuropsychopharmacology.* 2001; 25:662-668], that 5-HT$_6$ receptors are modulators of the whole number of neuromediator systems including cholinergic, noradrenergic, glutamatergic and dopaminergic. Taking into account the fundamental role of these systems in normal cognitive processes and their dysfunction at neurodegeneration, exclusive role of 5-HT$_6$ receptors in forming normal and "pathological" memory becomes obvious.

It was shown in a large number of nowadays publications that blocking of 5-HT$_6$ receptors leads to considerable enhancement of memory consolidation in various animal models of training-memorizing-reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100. Riemer C., Borroni E., Levet-Trafit B., Martin J. R., Poli S., Porter R. H., Bos M. Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-HT$_6$ receptor antagonist. *J. Med. Chem.* 2003; 46:1273-1276. King M. V., Woolley M. L., Topham I. A., Sleight A. J., Marsden C. A., Fone K. C. 5-HT6 receptor antagonists reverse delay-dependent deficits in novel object discrimination by enhancing consolidation of an effect sensitive to NMDA receptor antagonism. Neuropharmacology 2004; 47:195-204]. It was also demonstrated that considerable enhancement of cognitive functions in aged rats in Morrison's water maze experiment took place under the action of 5-HT$_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100]. Recently more thorough understanding of 5-HT$_6$ receptor function in cognitive processes and more accurate conceptions concerning possible pharmacophoric properties of their antagonists were achieved. [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. This resulted in preparation of highly affine selective ligands ("molecular tools"), and afterwards clinical candidates. At present a number of 5-HT$_6$ receptor antagonists are at various phases of clinical investigation as potential ingredients for treatment of AD, Huntington's disease, schizophrenia (antipsychotic) and other neurodegenerative and cognitive diseases (Table 1) [http://integrity.prous.com].

TABLE 1

5-HT$_6$ Receptor antagonists as drug candidates.

| Medicament | Clinical phase of testing | Developer | Therapeutic group |
| --- | --- | --- | --- |
| Dimebon ™ | Phase III | Medivation (USA) | Alzheimer's disease treatment |
| SGS-518 | Phase II | Lilly, Saegis | Cognitive diseases treatment |
| SB-742457 | Phase II | GlaxoSmithKline | Alzheimer's disease treatment; Antipsychotic |
| Dimebon* | Phase I/IIa | Medivation (USA) | Huntington's disease treatment |
| Dimebon* | Phase II | (Russia) | Schizophrenia |
| PRX-07034 | Phase I | Epix Pharm. | Obesity treatment; Antipsychotic; Cognitive diseases treatment |
| SB-737050A | Phase II | GlaxoSmithKline | Antipsychotic |
| BVT-74316 | Phase I | Biovitrum | Obesity treatment |

TABLE 1-continued

5-HT$_6$ Receptor antagonists as drug candidates.

| Medicament | Clinical phase of testing | Developer | Therapeutic group |
|---|---|---|---|
| SAM-315 | Phase I | Wyeth Pharm. | Alzheimer's disease treatment |
| SYN-114 | Phase I | Roche, Synosis Ther. | Cognitive diseases treatment |
| BGC-20-761 | Preclinical | BTG (London) | Antipsychotic; Cognitive diseases treatment |
| FMPO | Preclinical | Lilly | Antipsychotic |
| Dimebon ™ | Preclinical | (Russia) | Insult treatment |

Another attractive property of 5-HT$_6$ receptor antagonists is their ability to suppress appetite that can lead to preparation on their basis of essentially novel remedies for overweight lowering and obesity treatment. [Vicker S. P., Dourish C. T. Serotonin receptor ligands and the treatment of obesity. *Curr. Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. Davies S. L. Drug discovery targets: 5-HT$_6$ receptor. *Drug Future.* 2005; 30:479-495], its mechanism is based on suppression of γ-aminobutyric acid signaling by 5-HT$_6$ receptor antagonists and increasing of α-melanocyte-stimulating hormone emission, that, finally, results in lowering of food demand [Woolley M. L. 5-HT$_6$ receptors. *Curr. Drug Targets CNS Neurol. Disord.* 2004; 3:59-79]. Now two antagonists of 5-HT$_6$ receptors are at the first phase of clinical testing as drug candidates for obesity treatment (Table 1) [http://integrity.prous.com].

In this context searching for new selective and effective serotonin 5-HT$_6$ receptor antagonists seems to be original and perspective approach to the development of novel drug substances for treating of a great number of neurological and neurodegenerative diseases and cognitive disorders.

There are many publications in scientific literature concerning various biologically active arylsulfonyl substituted azaheterocycles, among them serotonin receptor ligands. For example, substituted 1-(2-aminoethyl)-4-(arylsulfonyl)pyrazoles of general formula A1 were described as serotonin 5-HT$_{2c}$ receptor ligands [WO 2003057674 A1] and substituted 7-amino-3-(arylsulfonyl)pyrazolo[1,5-a]pyrimidines A2 as serotonin 5-HT$_6$ receptor antagonists [EP 941994 A1, 1999]

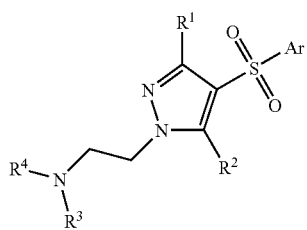

A1

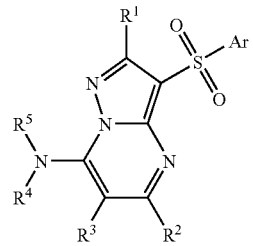

A2

A1: Ar=alkyl, aryl; R$^1$ and R$^2$=H, OH, alkyl, alkoxy; R$^3$ and R$^4$=H, alkyl, aryl.
A2: Ar=aryl, heterocyclyl; R$^1$=H, alkyl, alkylthio; R$^2$=H, alkyl, halogen; R$^3$=H, alkyl, hydroxyalkyl; R$^4$ and R$^5$=H; NR$^4$R$^5$=piperazinyl.

With the aim of working out novel highly effective neuroprotective medicaments the authors of the invention carried out widespread investigation in the field of substituted 3-(arylsulfonyl)pyrazolo[1,5-a]pyrimidines, as a result of which novel drug substances which were 5-HT$_6$ receptor antagonists have been found.

DISCLOSURE OF THE INVENTION

In the context of the invention, the terms are generally defined as follows.

"Agonists" mean ligands being bound to receptors of definite type actively promote transferring their specific signal and by that cause the biological response of the cell.

"Azaheterocycle" means aromatic or nonaromatic mono- or polycyclic system with at least one nitrogen atom. Azaheterocycles may have one or more "cyclic system substituents".

"Alkyl" means aliphatic hydrocarbon straight or branched group with 1-12 carbon atoms. Branched means alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or R$_k^a$R$_{k+1}^a$N—, R$_k^a$R$_{k+1}^a$NC(=O)—, R$_k^a$R$_{k+1}^a$NC(=S)—, R$_k^a$R$_{k+1}^a$NSO$_2$—, where R$_k^a$ and R$_{k+1}^a$ independently of each other represent "amino group" substituent, the meanings thereof are defined in this section, for example, hydrogen, alkyl, aryl, aralkyl, heteroaralkyl, heterocyclyl or heteroaryl, or R$_k^a$ and R$_{k+1}^a$ together with the N-atom, they are attached to, form through R$_k^a$ and R$_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^a R_{k+1}{}^a N—$, $R_k{}^a R_{k+1}{}^a NC(=O)—$, annelated arylheterocyclenyl, annelated arylheterocyclyl.

"Alkoxy" means alkyl-O-group, wherein alkyl is defined in this section. The preferred alkoxy groups are methoxy, ethoxy, n-propoxy, iso-propoxy and n-butoxy.

"Anxiolytic" (tranquilizer) means medicament intended for treatment of anxious disorders.

"Annelated cycle" (condensed cycle) means bi- or poly-cyclic system wherein annelated cycle and cycle or polycycle with which it is annelated has at least two common atoms.

"Antagonists" mean ligands being bound to definite receptors do not cause active cellular responses. Antagonists prevent linkage between agonists and receptors and by that block specific receptor signal transmission.

"Antidepressant" means medicament intended for treating depression.

"Antipsychotic" means remedy intended for treatment of psychotic diseases.

"Aryl" means aromatic mono- or polycyclic system with 6-14 carbon atoms, predominantly from 6 to 10 C-atoms. Aryl may have one or more "cyclic system substituents" of the same or different structure. Phenyl, substituted phenyl, naphthyl, or substituted naphthyl are the representatives of aryl groups. Aryl could be annelated with nonaromatic cyclic system or heterocycle.

"Arylsulfonyl" means aryl-$SO_2$-group, wherein meaning of aryl is defined in this section.

"Hydrate" means stoichiometric or nonstoichiometric compositions of the compounds or their salts with water.

"Depression" means big depression; incidental, chronic and recurring form of big depression; dysthymic disorder (dysthymia); cyclotymia; affective disorder; syndrome of seasonal affective disorder; bipolar disorder, including bipolar disorders of I and II type; and other depressive disorders and conditions. Depression also means the depressions accompanying AD, vascular dementia; disorder of mood induced by alcohol and substances; schizoaffective disorder of depressive type; disorder of adaptation. Except for that, depression includes depression of oncological patients; depression at Parkinson's disease; depressions after myocardial infarction; depressions of fruitless women; pediatric depression; postnatal depression; the depressions accompanying somatic, neuralgic and other diseases "Substituent" means chemical radical attached to scaffold (fragment), for example, "alkyl substituent", "amino group substituent", "carbamoyl substituent", and "cyclic system substituent", the meanings thereof are defined in this section.

"Alkyl group substituent" means substituent attached to alkyl or alkenyl group, the meanings of which are defined in this section. Alkyl group substituent is selected from hydrogen, alkyl, halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonyl, heteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k{}^a R_{k+1}{}^a N—$, $R_k{}^a R_{k+1}{}^a NC(=O)—$, $R_k{}^a R_{k+1}{}^a NSO_2—$, where $R_k{}^a$ and $R_{k+1}{}^a$ independently of each other represent "amino group substituent", the meanings of which are defined in this section, for example, hydrogen, alkyl, aryl, aralkyl, heteroaralkyl, heterocyclyl or heteroaryl, or $R_k{}^a$ and $R_{k+1}{}^a$ together with N-atom they are attached to via $R_k{}^a$ and $R_{k+1}{}^a$ form 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl, and pyridylmethyloxycarbonylmethyl. The preferred "alkyl group substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^a R_{k+1}{}^a N—$, $R_k{}^a R_{k+1}{}^a NC(=O)—$, annelated arylheterocyclenyl, annelated arylheterocyclyl. The meanings of "alkyl group substituents" are defined in this section.

"Cognitive disorders or disorders of cognitive functions" mean disorders (weakening) of mental abilities including attentiveness, memory, mentality, cognition, education, verbal, mental, executive and creative abilities, time and space orientation; in particular, cognitive disorders associated with AD, Parkinson's and Huntington's diseases, senile dementia; age-associated memory impairment, AAMI; dysmetabolic encephalopathy; psychogenous memory impairment; amnesia; amnesic disturbances; transit global amnesia; dissociative amnesia; vascular dementia; light or mild cognitive impairment (MCI); attention deficit hyperactivity disorder (AD/HD); cognitive impairments, accompanying psychotic diseases, epilepsy, delirium, autism, psychosis, Down's syndrome, bipolar disorders and depression; AIDS-associated dementia; dementias at hypothyroidism; dementia connected with alcohol, substances causing dependability and neurotoxins; dementia accompanying neurodegenerative diseases, for example, cerebella degeneracy and amyotrophic lateral sclerosis; cognitive disturbances connected with cerebral crisis, infectious and oncological brain diseases as well as traumatic brain injury; cognitive function damages associated with autoimmune and endocrine diseases, and others.

"Drug substance" means physiologically active compound of synthetic or other (biotechnological, vegetable, animal, microbe and so on) origin exhibiting pharmacological activity and being an active ingredient of pharmaceutical composition employed in production and preparation of medicaments.

"Medicament"—is compound or mixture of compounds representing pharmaceutical composition in the form of tablets, capsules, injections, ointments and other drug products intended for restoration, improvement or modification of physiological functions at humans and animals, and for treatment and prophylaxis of diseases, diagnostics, anesthesia, contraception, cosmetology and others.

"Ligands" (from Latin ligo) represent chemical compounds (small molecule, peptide, protein, inorganic ion, and so on) capable to interact with receptors which convert this interaction into specific signal.

"Neurodegenerative diseases" means specific conditions and diseases, accompanied by damage and primary destruction of nervous cell populations in certain areas of central nervous system. Neurodegenerative diseases include but are not limited by: AB; Parkinson's and Huntington's diseases (chorea); multiocular sclerosis; cerebella degeneracy; amyotrophic lateral sclerosis; dementias with Lewy bodies; spinal muscular atrophy; peripherical neuropathy; spongy encephalitis (Creutzfeld-Jakob Disease); AIDS dementia; multi-infract dementia; frontotemporal dementias; leukoencephalopathy (spongy degeneration of white matter); chronic neurodegenerative diseases; cerebral crisis; ischemic, reperfusion and hypoxic brain damage; epilepsy; cerebral ischemia; glaucoma; traumatic brain injury; Down's syndrome; encephalomyelitis; meningitis; encephalitis; neuroblastoma; schizophrenia; depression. Moreover, neurodegenerative diseases include pathological states and disorders associated with hypoxia, substance abuse, causing dependability, under neurotoxins influence; infectious and oncological brain diseases as well as neuronal damages associated with autoimmune and endocrine diseases and others.

"Nootrops" or "Nootropics" (neurometabolic stimulates) are medicaments taken for cognition enhancing.

"Psychic disorders, (psychic diseases)" are diseases or diseased states associated with mental disturbance and/or mentality frustration. "Psychic disorders" include affective disorders (bipolar affective disorders, big depression, hypomania, minor depression, maniacal syndrome, Cotard's syndrome, cyclothymia, schizoaffective disorders and so on), intellectual-mnestic disorders; manias (hypomania, graphomania, kleptomania, compulsive shopping, mania of persecution, pornographomania, erotomania and so on); disorder of multiple personality, amentia, alcoholomania, deliration, delirium syndrome, hallucinosis, hallucinations, lucinatory effects, homicidomania, delirium; illusion, querulous paranoiaclinical lycanthropy, macropsia, antagonistic delusion, micropsia, narcomania; anorexia nervosa, oneiroid syndrome, paranoid, paranoia, paraphrenia, pseudohallucinations, psychosis, Cotard's syndrome, schizoaffective disorder, schizotypical disorder, schizophrenia, schizoaffective psychosis disorder, schizophrenomorphic disorder, Shrebera's syndrome, Daniel Paul's syndrome), phobias (agarophobia, arachnephobia, autophobia, verminophobia, hydrosophobia, hydrophobia, demophobia, zoophobia, carcinophobia, claustrophobia, climacophobia, xenophobia, misophobia, radiophobia, photophobia; skoliephobia, scotophobia, social phobia, tetraphobia, triskaidekaphobia, erotophobia); alcoholic psychosis, alcoholic palimpsest, allotriophagy, aphasia, graphomania, dissociative fugue state, dissociative disorders; dysphorias, internet-dependences, hypochondria, hysteria, kopophobia, delirium of persecution, melancholy, misanthropy, obsession, panic attacks, Asperger's syndrome, Capgras' syndrome, Munchausen's syndrome, Retta's syndrome, Fregoly's syndrome, syndrome of attention and hyperactivity deficit, obsessive-compulsive disorder, syndrome of chronic narcotization consequences, syndrome of psychic automatism, syndrome of infantile autism, madness, taphophilia, anxiety conditions, Hikikomory's syndrome, erotographomania and so on.

"Psychotic diseases" are all types of schizophrenia; schizoaffective psychosis; schizotypical disorders; schizoaffective disorders, including bipolar and depressive types; delirious disorders including reference delusion, delusion of persecution, megalomania, delusion of jealousy, erotomania, and also hypochondriacal, somatic, mixed and not differentiated delirium; short-time psychotic disorders; induced psychotic frustration; induced by substances psychotic frustration; and other psychotic disorders.

"Receptors" (from Latin recipere) represent biological macromolecules located either on cytoplasm membrane of cell or intracellular, capable specifically interact with restricted number of physiologically active compounds (ligands) and transform the signal of this interaction into definite cellular response.

"Therapeutic kit" is simultaneously administered combination of two or more drug substances with different mechanism of pharmacological action and aimed at different biotargets taking part in pathogenesis of the disease.

"Anxiety disorders" means generalized (inconcrete) anxiety; acute uncontrolled anxiety; panic disorder; phobia, for example, agorophobia (acute fear of crowded place) or social (acute fear of humiliation at presence of other people) or any other phobia (acute fear of particular subjects, animals or situations, in the form of phobia of height, of medical procedures, lifts, open space etc.); an obsessional condition (obsessive-compulsive disorder); posttraumatic stress disorder and acute stress disorder. Besides, anxiety disorders include anxiety conditions induced by alcohol or substances; anxiety under adaptation; as well as mixed forms of anxiety disorders and depression.

"Pharmaceutical composition" means composition comprising, at least, one of compounds of general formula 1 and, at least, one of the components selected from pharmaceutically acceptable and pharmacologically compatible fillers, solvents, diluents, auxiliary, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dosage. Examples of suitable suspending agents are: ethoxylated isostearyl alcohol, polyoxyethene, sorbitol and sorbitol ether, microcrystalline cellulose, aluminum metahydroxide, bentonite, agar-agar and tragacant and mixtures thereof as well. Protection against microorganism action can be provided by various antibacterial and antifungal agents, such as: parabens, chlorobutanol, sorbic acid, and similar compounds. Composition may also contain isotonic agents, such as: sugar, sodium chloride, and similar compounds. Prolonged effect of the composition may be achieved by agents slowing down absorption of the active ingredient, for example, aluminum monostearate and gelatin. Examples of suitable carriers, solvents, diluents and delivery agents include water, ethanol, polyalcohols and their mixtures, natural oils (such as olive oil) and injection-grade organic esters (such as ethyl oleate). Examples of fillers are: lactose, milk-sugar, sodium citrate, calcium carbonate, calcium phosphate and the like. Examples of disintegrators and distributors are: starch, alginic acid and its salts, and silicates. Examples of suitable lubricants are: magnesium stearate, sodium lauryl sulfate, talc and polyethylene glycol of high molecular weight. Pharmaceutical composition for peroral, sublingual, transdermal, intramuscular, intravenous, subcutaneous, local or rectal administration of active ingredient, alone or in combination with another active compound, may be administered to humans and animals in standard administration form, or mixture with traditional pharmaceutical carriers. Suitable standard administration forms include peroral forms such as tablets, gelatin capsules, pills, powders, granules, chewing-gums and peroral solutions or suspensions, for example, therapeutic kit; sublingual and transbuccal administration forms; aerosols; implants; local, transdermal, subcutaneous, intramuscular, intravenous, intranasal or intraocular forms and rectal administration forms.

"Pharmaceutically acceptable salt" means relatively nontoxic both organic and inorganic salts of acids and bases disclosed in this invention. Salts could be prepared in situ in processes of synthesis, isolation or purification of compounds or prepared specially. In particular, salts of bases could be prepared starting from purified bases disclosed in the invention and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of such salt properties is given in: Berge S. M., et al., "Pharmaceutical Salts" J. Pharm. Sci., 1977, 66: 1-19). Salts of disclosed acids may be prepared by reaction of purified acids with suitable base; moreover, metal salts and amine salts may be synthesized too. Metal salts are salts of sodium, potassium, calcium, barium, magnesium, lithium and aluminum; sodium and potassium salts being preferred. Suitable inorganic bases from which metal salts can be prepared are: sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of disclosed acid salts are amines and amino acids the basicity of which is sufficient enough to produce stable salt and suitable for use in medical purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as: holine, tetramethylammonium, tetraethylammonium, and the like Amino acids may be selected from the main amino acids—lysine, ornithine and arginine.

"Cycloalkyl" means nonaromatic mono- or polycyclic system with 3-10 carbon atoms. Cycloalkyl may have one or more "cyclic system substituents" of the same or different structure. Representatives of cycloalkyl groups are: cyclopropyl, cyclobutyl, cyclopentyl, cyclohexyl, decalinyl, norbornyl, adamant-1-yl and others. Cycloalkyl could be annelated with aromatic cycle or heterocycle. The preferred "cyclic system substituents" are alkyl, aralkoxy, hydroxy or $R_k{}^a R_{k+1}{}^a N$— the meanings of which are defined in this section.

"Schizophrenia" means all known types, forms and variants of the disease, including: simple, hebephrenic, paranoid, hypertoxic (pyretic), catatonic, schizoaffective, residual or not differentiated schizophrenia and/or the forms of schizophrenia defined in classification of American Psychiatric Association (*American Psychiatric Association; in: Diagnostic and Statistical Manual of Mental Disorders*, IV Edition, Washington D.C. 2000) or in International classification (*International Statistical Classification of Diseases and Related Health Problems*) or any other known forms.

The purpose of the present invention is novel 3-(arylsulfonyl)pyrazolo[1,5-a]pyrimidines, novel serotonin 5-HT$_6$ receptor antagonists, novel drug substances and pharmaceutical compositions, comprising the said novel compounds as drug substances, novel medicaments and methods for prophylaxis and treatment of various diseases of central nerves system, among them cognitive and neurodegenerative diseases.

The purpose in view is achieved by substituted 2-alkylamino-3-(arylsulfonyl)-cycloalkyl[e]pyrazolo[1,5-a]pyrimidines of general formula 1 and substituted 2-alkylamino-3-(arylsulfonyl)-cycloalkyl[d]pyrazolo[1,5-a]pyrimidines of general formula 2

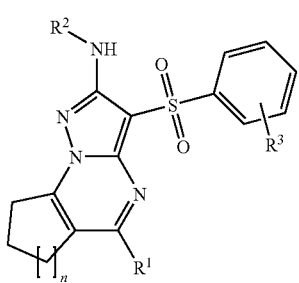

1

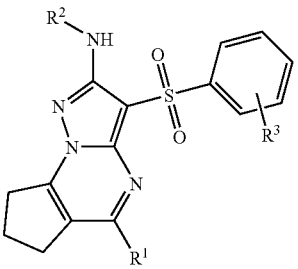

2 wherein:
$R^1$ represents hydrogen or $C_1$-$C_3$ alkyl;
$R^2$ represents $C_1$-$C_3$ alkyl;
$R^3$ represents hydrogen atom, one or two optionally identical halogen atoms, $C_1$-$C_3$ alkyl or hydroxy group optionally substituted with $C_1$-$C_3$ alkyl;
n represents the whole numbers 1, 2 or 3.

The preferred serotonin 5-HT$_6$ receptor antagonists are 2-alkylamino-3-(arylsulfonyl)-7,8-dihydro-6H-cyclopenta[e]pyrazolo[1,5-a]pyrimidines of general formula 1.1, 2-alkylamino-3-(arylsulfonyl)-6,7,8,9-tetrahydro-cyclohexa[e]pyrazolo[1,5-a]pyrimidines of the general formula 1.2 and 2-alkylamino-3-(arylsulfonyl)-7,8,9,10-tetrahydro-6H-cyclohepta[e]pyrazolo[1,5-a]pyrimidines of general formula 1.3,

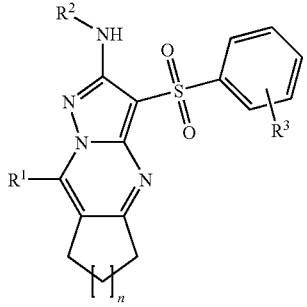

1.1

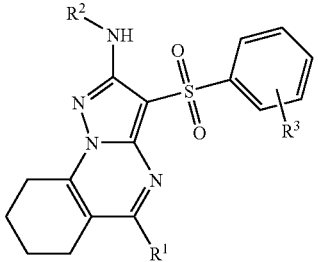

1.2

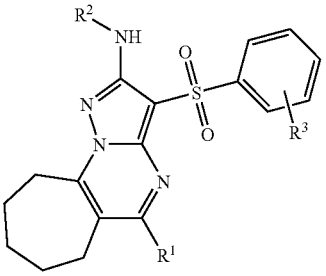

1.3 wherein:
$R^1$, $R^2$ and $R^3$ are all as defined above.

The preferred serotonin 5-HT$_6$ receptor antagonists are: 2-methylamino-3-(phenylsulfonyl)-7,8-dihydro-6H-cyclopenta[e]pyrazolo[1,5-a]pyrimidine 1.1(1), 2-methylamino-3-(3-chlorophenylsulfonyl)-7,8-dihydro-6H-cyclopenta[e]pyrazolo[1,5-a]pyrimidine 1.1(2), 5-methyl-2-methylamino-3-(phenylsulfonyl)-7,8-dihydro-6H-cyclopenta[e]pyrazolo[1,5-a]pyrimidine 1.1(3), 5-methyl-2-methylamino-3-(3-chlorophenylsulfonyl)-7,8-dihydro-6H-cyclopenta[e]pyrazolo[1,5-a]pyrimidine 1.1(4), 2-methylamino-3-(phenylsulfonyl)-6,7,8,9-tetrahydrocyclohexa[e]pyrazolo[1,5-a]pyrimidine 1.2(1), 2-methylamino-3-(3-chlorophenylsulfonyl)-6,7,8,9-tetrahydrocyclohexa[e]pyrazolo[1,5-a]pyrimidine 1.2(2), 5-methyl-2-methylamino-(3-phenylsulfonyl)-6,7,8,9-tetrahydrocyclohexa[e]pyrazolo[1,5-a]pyrimidine 1.2(3), 5-methyl-2-methylamino-3-(3-fluorophenylsulfonyl)-6,7,8,9-tetrahydrocyclohexa[e]pyrazolo[1,5-a]pyrimidine 1.2(4), 5-methyl-2-methylamino-3-(3-chlorophenylsulfonyl)-6,7,8,9-tetrahydrocyclohexa[e]pyrazolo[1,5-a]pyrimidine 1.2(5), 5-methyl-2-methylamino-3-(3-chloro-4-fluorophenylsulfonyl)-6,7,8,9-tetrahydrocyclohexa[e]pyrazolo[1,5-a]pyrimidine 1.2(6), 2-methylamino-3-(phenylsulfonyl)-7,8,9,10-tetrahydro-6H-cyclohepta[e]pyrazolo[1,5-a]pyrimidine 1.3(1) and 2-methylamino-3-(3-chlorophenylsulfonyl)-7,8,9,10-tetrahydro-6H-cyclohepta[e]pyrazolo[1,5-a]pyrimidine 1.3(2)

1.1(1)
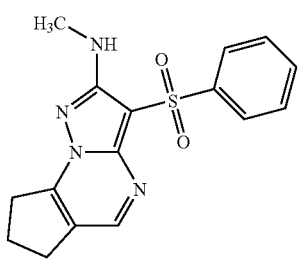 [SMILES: CNc1nn2c3c(cnc2c1S(=O)(=O)c1ccccc1)CCC3]

1.1(2)
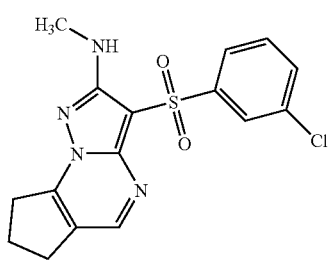 [SMILES: CNc1nn2c3c(cnc2c1S(=O)(=O)c1cccc(Cl)c1)CCC3]

1.1(3)
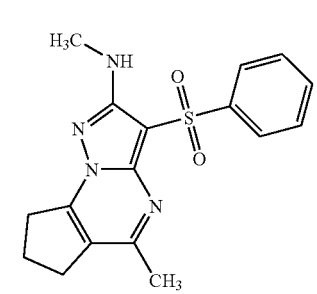 [SMILES: CNc1nn2c3c(c(C)nc2c1S(=O)(=O)c1ccccc1)CCC3]

1.1(4)
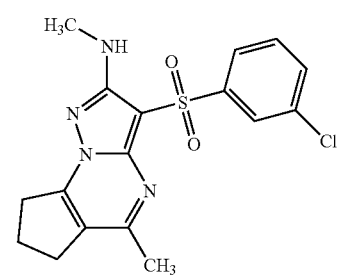 [SMILES: CNc1nn2c3c(c(C)nc2c1S(=O)(=O)c1cccc(Cl)c1)CCC3]

1.2(1)
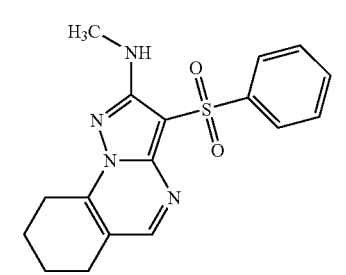 [SMILES: CNc1nn2c3c(cnc2c1S(=O)(=O)c1ccccc1)CCCC3]

1.2(2)
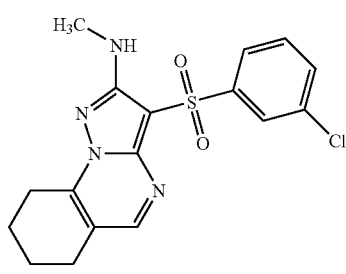 [SMILES: CNc1nn2c3c(cnc2c1S(=O)(=O)c1cccc(Cl)c1)CCCC3]

1.2(3)
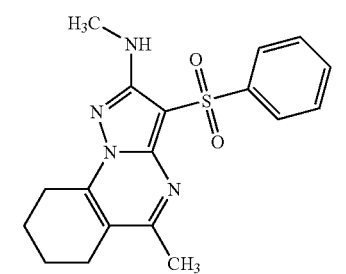 [SMILES: CNc1nn2c3c(c(C)nc2c1S(=O)(=O)c1ccccc1)CCCC3]

1.2(4)
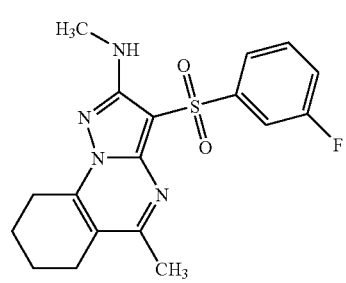 [SMILES: CNc1nn2c3c(c(C)nc2c1S(=O)(=O)c1cccc(F)c1)CCCC3]

1.2(5)
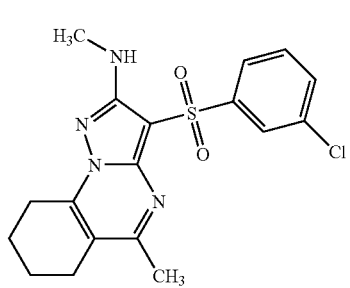 [SMILES: CNc1nn2c3c(c(C)nc2c1S(=O)(=O)c1cccc(Cl)c1)CCCC3]

-continued

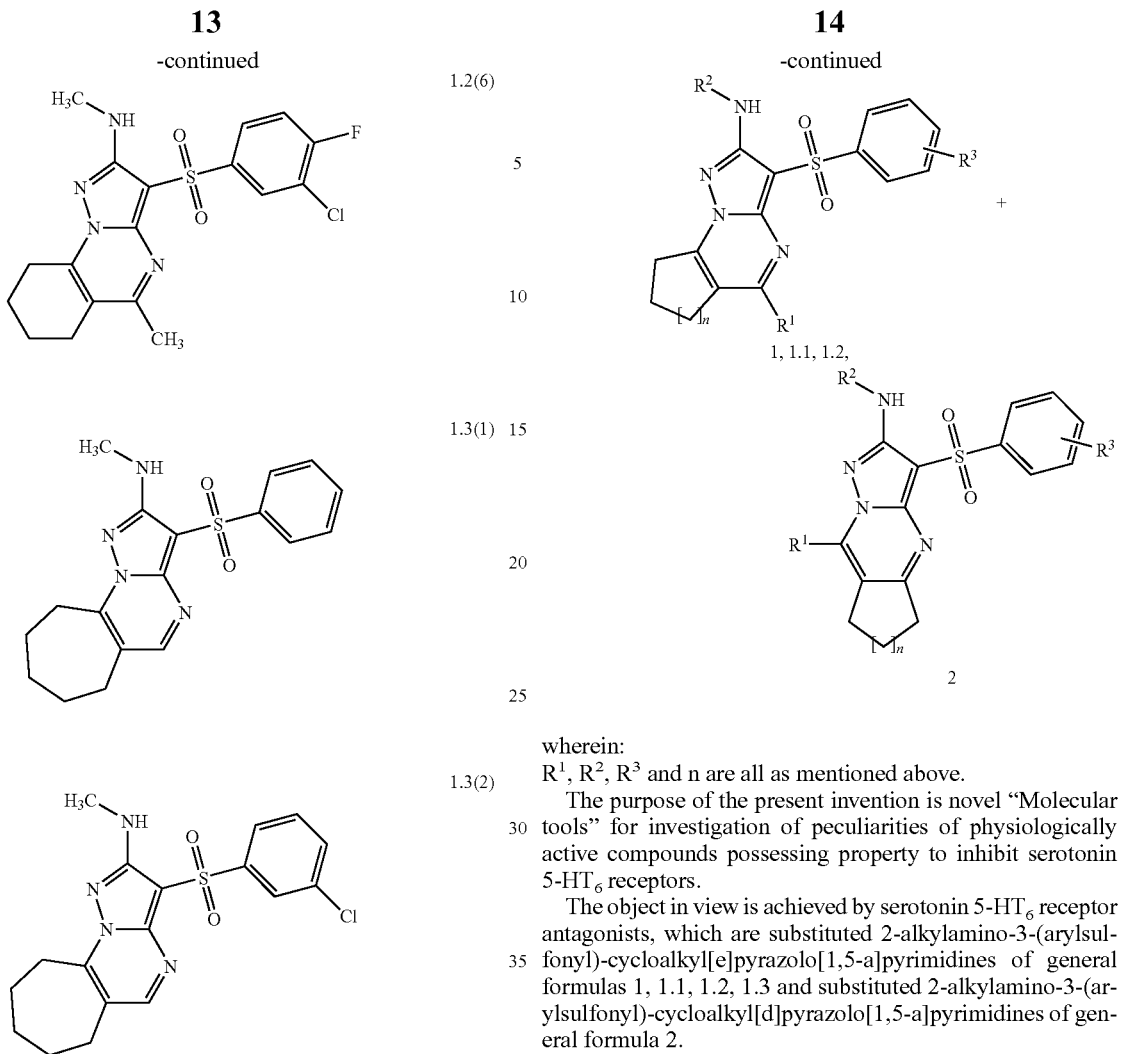

1, 1.1, 1.2,

2 wherein:
$R^1$, $R^2$, $R^3$ and n are all as mentioned above.

The purpose of the present invention is novel "Molecular tools" for investigation of peculiarities of physiologically active compounds possessing property to inhibit serotonin 5-$HT_6$ receptors.

The object in view is achieved by serotonin 5-$HT_6$ receptor antagonists, which are substituted 2-alkylamino-3-(arylsulfonyl)-cycloalkyl[e]pyrazolo[1,5-a]pyrimidines of general formulas 1, 1.1, 1.2, 1.3 and substituted 2-alkylamino-3-(arylsulfonyl)-cycloalkyl[d]pyrazolo[1,5-a]pyrimidines of general formula 2.

The purpose of the present invention is drug substance for pharmaceutical compositions and medicaments, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2.

The subject of the present invention is pharmaceutical composition for prophylaxis and treatment of various conditions and diseases of CNS at humans and warm-blooded animals, comprising pharmaceutically effective amount of a novel drug substance which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2.

Pharmaceutical compositions may include pharmaceutically acceptable excipients. Pharmaceutically acceptable excipients mean diluents, auxiliary agents and/or carriers applied in the sphere of pharmaceutics. According to the invention pharmaceutical composition together with drug substance of general formula 1 may include other active ingredients provided that they do not give rise to undesirable effects, such as allergic reactions.

If needed, according to the present invention pharmaceutical compositions could be used in clinical practice in various forms prepared by mixing the said compositions with traditional pharmaceutical carries, for example, peroral forms (such as, tablets, gelatinous capsules, pills, solutions or suspensions); forms for injections (such as, solutions or suspen- The purpose of the present invention is method for preparation of substituted 2-alkylamino-3-(arylsulfonyl)-cycloalkyl[e]pyrazolo[1,5-a]pyrimidines of general formulas 1, 1.1, 1.2, 1.3 and substituted 2-alkylamino-3-(arylsulfonyl)-cycloalkyl[d]pyrazolo[1,5-a]pyrimidines of general formula 2 by interaction of 3-amino-4-arylsulfonyl-2H-pyrazoles of general formula 3 with corresponding β-dicarbonyl compounds of general formula 4 or their derivatives of general formula 5 and subsequent isolation or separation of the reaction products of general formulas 1, 1.1, 1.2, 1.3, 2 according to scheme given below.

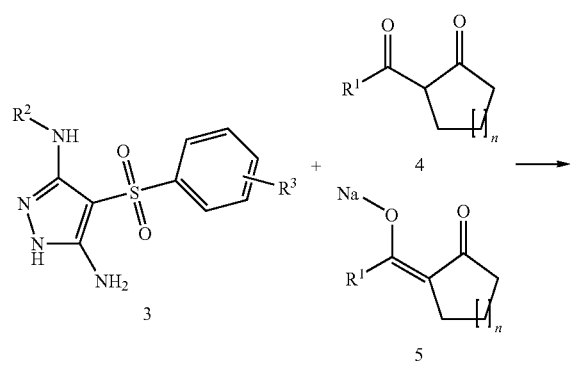

sions for injections, or a dry powder for injections which requires only addition of water for injections before utilization); local forms (such as, ointments or solutions).

According to the present invention the carriers used in pharmaceutical compositions represent carriers which are used in the sphere of pharmaceutics for preparation of commonly used forms. Binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The subject of the present invention is also method for preparation of pharmaceutical composition by mixing a drug substance which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2 with inert exicipient and/or solvent.

The subject of the present invention is also medicament in the form of tablets, capsules, or injections, placed in pharmaceutically acceptable packing intended for treatment and prophylaxis of cognitive disorders and neurodegenerative diseases, pathogenesis of which is associated with 5-HT$_6$ receptors, comprising pharmaceutically effective amount of drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The preferable medicament is medicament in the form of tablets, capsules, or injections, placed in pharmaceutically acceptable packing intended for treatment and prophylaxis of AD, Parkinson's and Huntington's diseases including pharmaceutically effective amount of drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The subject of the present invention is medicament in the form of tablets, capsules, or injections, placed in pharmaceutically acceptable packing intended for treatment and prophylaxis of psychotic disorders and schizophrenia comprising pharmaceutically effective amount of a drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The preferable medicament is medicament (anxiolytic or tranquillizer) intended for treatment and prophylaxis of anxiety disorders, comprising pharmaceutically effective amount of a drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The preferable medicament is medicament (nootropics) intended for treatment and prophylaxis of hyperkinetic disorders, more specifically, for mental ability enhancing, comprising pharmaceutically effective amount of a drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The purpose of the present invention is medicament in the form of tablets, capsules, or injections, placed in pharmaceutically acceptable packing intended for treatment and prophylaxis of obesity, comprising pharmaceutically effective amount of a drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The subject of the present invention is therapeutic kit intended for treatment and prophylaxis of various diseases pathogenesis of which is associated with serotonin 5-HT$_6$ receptors at humans and animals, including medicament which comprises pharmaceutically effective amount of a drug substance, which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

The subject of the present invention is therapeutic kit intended for treatment and prophylaxis of neurological disorders, neurodegenerative and cognitive diseases at humans and animals, among them AD, Parkinson's and Huntington's diseases, psychotic disorders, schizophrenia, hypoxia-ischemia, hypoglycemia, convulsive states, brain injuries, lathyrism, amyotrophic lateral sclerosis, obesity or insult, including medicament which comprises pharmaceutically effective amount of a drug substance, which is, at least, one of 2-alkylamino-3-(arylsulfonyl)-cycloalkyl[e]pyrazolo[1,5-a] pyrimidines of general formulas 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance.

Therapeutic kit for prophylaxis and treatment of neurological disorders, neurodegenerative and cognitive diseases at humans and animals, among them for treatment and prophylaxis of AD, Parkinson's and Huntington's disease, psychotic disorders, schizophrenia, hypoxia-ischemia, hypoglycemia, convulsive states, brain injuries, lathyrism, amyotrophic lateral sclerosis, obesity or insult, along with drug substances disclosed in the invention, may include other active ingredients such as: nonsteroidal anti-inflammatory drugs (Orthophene, Indomethacin, Ibuprophen and others); acetyl cholinesterase inhibitors (Tacrine, Amiridine, Fizostigmine, Aricept, Phenserine and others); estrogens (for example, Estradiol); NMDA-receptor antagonists (for example, Memantine, Neramexane); nootropic drugs (for example, Pyracetam, Fenibut and others); AMPA receptor modulators (for example, Ampalex); antagonists of cannabinoid receptors CB-1 (for example, Rimonabant); monoaminooxidase inhibitors MAO-B and/or MAO-A (for example, Rasagiline); antiamyloidogenic drugs (for example, Tramiprosate); lowering β-amyloidal neurotoxicity compounds (for example, Indole-3-propionic acid); γ- and/or β-secretase inhibitors; M1-muscarinic receptor agonists (for example, Cevimeline); metal helates (for example, Clioquinol); GABA(A) receptor antagonists (for example, CGP-36742); monoclonal antibodies (for example, Bapineuzumab); antioxidants; neurotrophic agents (for example, Cerebrolisine); antidepressants (for example, Imipramine, Sertraline and others) and others.

The therapeutic kit for overweight lowering and obesity treatment along with drug substances disclosed in the invention, may include other active ingredients such as: anorectic drugs (for example, Fepranon, Desopimon, Masindole), hormone drugs (for example, Tireoidine), hypolipidemic means such as fibrates (for example, Fenofibrate), statines (for example, Lovastatine, Simvastatine, Pravastatine and Probucol), and also hypoglycemic drugs (sulfonylurea—for example, Butamide, Glibenclamide; biguanidines—for example, Buformine, Metamorphine) and drugs with some other mechanism of action, such as cannabinoid CB-1 receptor antagonists (Rimonabant), inhibitors of norepinephrine and serotonin reuptake (Sibutramine), inhibitors of ferments of fatty acids synthesis (Orlistat) and others, along with antioxidants, food additives and others.

According to the present invention method for prophylaxis and treatment of various diseases pathogenesis of which is associated with serotonin 5-$HT_6$ receptors at humans and animals, consists in introduction of novel medicament in the form of tablets, capsules, or injections, placed in pharmaceutically acceptable packing comprising pharmaceutically effective amount of an active ingredient which is, at least, one of 2-alkylamino-3-(arylsulfonyl)-cycloalkyl[e]pyrazolo[1,5-a]pyrimidines of general formulas 1, 1.1, 1.2, 1.3 or 2-alkylamino-3-(arylsulfonyl)-cycloalkyl[d]pyrazolo[1,5-a]pyrimidines of general formula 2 or pharmaceutical composition including this drug substance. Medicament could be introduced peroral or parenterally (for example, intravenously, subcutaneously, intraperitoneally or locally). Clinical dose of pharmaceutical composition or medicament comprising drug substance may be corrected depending on: therapeutic efficiency and bio-accessibility of active ingredients in patients' organism, rate of their exchange and removal from organism, and age, gender, and severity of patient's symptoms. Thus, the daily intake for adults normally being 10500 mg, preferably 50~300 mg. Accordingly, the above effective doses are to be taken into consideration while preparing medicament of the present invention, each dose unit of the medicament contains 10~500 mg of drug substance which is, at least, one of 2-alkylamino-3-(arylsulfonyl)-cycloalkyl[e]pyrazolo[1,5-a]pyrimidines of general formula 1, 1.1, 1.2, 1.3 or 2-alkylamino-3-(arylsulfonyl)-cycloalkyl[d]pyrazolo[1,5-a]pyrimidines of general formula 2, or pharmaceutical composition comprising this drug substance, preferably 50~300 mg. Following the instructions of physician or pharmacist, the medicaments may be taken several times over specified periods of time (preferably, from one to six times).

BEST EMBODIMENT OF THE INVENTION

Below the invention is described by means of specific examples, which illustrate but not limit the scope of the invention.

Example 1

General method for preparation of substituted 2-alkylamino-3-(arylsulfonyl)-cycloalkyl[e]pyrazolo[1,5-a]pyrimidines of general formulas 1, 1.1, 1.2, 1.3 and 2-alkylamino-3-(arylsulfonyl)-cycloalkyl[d]pyrazolo[1,5-a]pyrimidines of general formula 2. Mixture of 0.005 mol of aminopyrazole 3 and 0.0055 mol of corresponding β-dicarbonyl compound of general formula 4 or its derivatives of general formula 5 in 5 ml of acetic acid or other suitable solvent was boiled for 4-12 hr. After cooling the solid precipitated was filtered off, washed with methanol and water. If necessary, the product was subjected to recrystallization from proper solvent, or chromatographic purification or chromatographic separation.

Table 2 represents some examples of novel 2-alkylamino-3-(arylsulfonyl)-cycloalkyl[e]pyrazolo[1,5-a]pyrimidines of general formulas 1, 1.1, 1.2, 1.3 and 2-alkylamino-3-(arylsulfonyl)-cycloalkyl[d]pyrazolo[1,5-a]pyrimidines of general formula 2, their LCMS and NMR data.

TABLE 2

Serotonin 5-$HT_6$ receptor antagonists—2-alkylamino-3-(arylsulfonyl)-cycloalkyl[e]pyrazolo[1,5-a]pyrimidines of general formula 1 and 2-alkylamino-3-(arylsulfonyl)-cycloalkyl[d]pyrazolo[1,5-a]pyrimidines of general formula 2.

| No | Formula | Mol. w. | LCMS, m/z (M + 1) | NMR |
|---|---|---|---|---|
| 1.1(1) | | 328.40 | 329 | (DMSO-$D_6$, 400 MHz) δ 8.44 (s, 1H), 8.00 (m, 2H), 7.56 (m, 3H), 6.43 (q, J = 4.8 Hz, 1H), 3.17 (t, J = 7.6 Hz, 2H), 2.96 (t, J = 7.6 Hz, 2H), 2.92 (d, J = 4.8 Hz, 3H), 2.15 (m, J = 7.6 Hz, 2H). |
| 1.1(2) | | 362.84 | 363 | |

TABLE 2-continued

Serotonin 5-HT$_6$ receptor antagonists—2-alkylamino-3-(arylsulfonyl)-cycloalkyl[e]pyrazolo[1,5-a]pyrimidines of general formula 1 and 2-alkylamino-3-(arylsulfonyl)-cycloalkyl[d]pyrazolo[1,5-a]pyrimidines of general formula 2.

| No | Formula | Mol. w. | LCMS, m/z (M + 1) | NMR |
|---|---|---|---|---|
| 1.1(3) | | 342.42 | 343 | (CDCl$_3$): 8.14 (d, J = 8 Hz, 2H); 7.37-7.52 (m, 3H); 6.01 (br.q, J = 4.5 Hz, 1H); 3.22 (t, J = 7.6 Hz, 2H); 3.02 (d, J = 4.5 Hz, 3H): 2.93 (t, J = 7.3 Hz, 2H); 2.51 (s, 3H); 2.18-2.28 (m, 2H). |
| 1.1(4) | | 376.87 | 377 | |
| 1.2(1) | | 342.42 | 343 | (DMSO-D$_6$, 400 MHz) δ 8.32 (s, 1H), 7.99 (d, J = 8 Hz, 2H), 7.59 (t, J = 7.2 Hz, 1H), 7.54 (t, J = 7.6 Hz, 2H), 6.37 (q, J = 4.8 Hz, 1H), 2.93 (m, 5H), 2.7 (t, J = 6 Hz, 2H), 1.84 (m, 2H), 1.73 (m, 2H). |
| 1.2(2) | | 376.87 | 377 | |
| 1.2(3) | | 356.45 | 357 | |

TABLE 2-continued

Serotonin 5-HT$_6$ receptor antagonists—2-alkylamino-3-(arylsulfonyl)-cycloalkyl[e]pyrazolo[1,5-a]pyrimidines of general formula 1 and 2-alkylamino-3-(arylsulfonyl)-cycloalkyl[d]pyrazolo[1,5-a]pyrimidines of general formula 2.

| No | Formula | Mol. w. | LCMS, m/z (M + 1) | NMR |
|---|---|---|---|---|
| 1.2(4) | | 374.44 | 375 | |
| 1.2(5) | | 390.89 | 391 | |
| 1.2(6) | | 408.89 | 409 | |
| 1.3(1) | | 356.45 | 357 | |
| 1.3(2) | | 390.89 | 391 | |

TABLE 2-continued

Serotonin 5-HT$_6$ receptor antagonists—2-alkylamino-3-(arylsulfonyl)-
cycloalkyl[e]pyrazolo[1,5-a]pyrimidines of general formula 1 and 2-alkylamino-3-
(arylsulfonyl)-cycloalkyl[d]pyrazolo[1,5-a]pyrimidines of general formula 2.

| No | Formula | Mol. w. | LCMS, m/z (M + 1) | NMR |
|---|---|---|---|---|
| 2(1) | [structure] | 342.42 | 343 | (DMSO-D$_6$, 400 MHz) δ 8.71 (s, 1H), 8.00 (d, J = 6.8 Hz, 2H), 7.57 (m, 3H), 6.32 (q, J = 4.8 Hz, 1H), 2.87 (m, 5H), 2.69 (t, J = 6.4 Hz, 2H), 2.53 (s, 3H), 1.82 (m, 2H), 1.72 (m, 2H). |
| 2(2) | [structure] | 356.45 | 357 | |

Example 2

Determination of antagonistic activity of compounds of general formula 1 towards 5-HT$_6$ receptors. Compounds of general formula 1 were tested for their ability to prevent 5-HT$_6$ receptors activation by serotonin. HEK 293 cells (cells of human embryo's kidney) with artificially expressed 5-HT$_6$ receptor, activation of which by serotonin leads to increasing the concentration of intracellular cAMP were used. The content of intracellular cAMP was determined using reagent kit LANCE cAMP (PerkinElmer) according to the method described by the manufacturer of the kit [http://las.perkinelmer.com/content/Manuals/MAN_LANCEcAMP384KitUser.pdf]. Effectiveness of compounds was estimated by their ability to reduce the content of intracellular cAMP induced by serotonin. Table 3 presents IC$_{50}$ values of serotonin 5-HT$_6$ receptor inhibition by antagonists of general formula 1 and 2 in the setting of functional assay. The data given testify their high antagonistic activity.

TABLE 3

IC$_{50}$ values of serotonin 5-HT$_6$ receptor inhibition by antagonists of general formula 1 and 2 in the setting of functional assay.

| Antagonists of general formulas 1 and 2 | IC$_{50}$, nM |
|---|---|
| 1.1(1) | 4.8 |
| 1.1(3) | 7.0 |
| 1.2(1) | 4.4 |
| 2(1) | 7.5 |
| 2(2) | 15.5 |

Example 3

Activity determination of serotonin 5-HT$_6$ receptor antagonists of the general formula 1 in the setting of competitive binding to serotonin 5-HT$_6$ receptors.

Screening of disclosed compounds for their potential ability to interact with serotonin 5-HT$_6$ receptors was carried out by method of radioligand binding. For this purpose membrane species were prepared from expressing recombinant human 5-HT$_6$ receptors HeLa cells by means of their homogenization in glass homogenizer with subsequent separation of plasmatic membranes from cell nuclei, mitochondria's and cell wreckages by differential centrifugation. Determination of tested compounds binding to 5-HT$_6$ receptors was carried out according to the method described in [Monsma F J Jr, Shen Y, Ward R P, Hamblin M W and Sibley D R, Cloning and expression of a novel serotonin receptor with high affinity for tricyclic psychotropic drugs. Mol Pharmacol. 43:320-327, 1993]. In the preferred embodiment membrane preparations were incubated with radioligand (1.5 nM [$^3$H] Lysergic acid diethylamide) without and in the presence of investigated compounds for 120 min at 37° C. in medium consisting of mM Tris-HCl, pH 7.4, 150 mM NaCl, 2 mM Ascorbic Acid, 0.001% BSA. After incubation the samples were filtered in vacuo on glass-microfiber filters G/F (Millipor, USA), filters were washed three times with cold solution of medium and radioactivity was measured by scintillation counter Micro-Beta 340 (PerkinElmer, USA). Nonspecific binding which made up 30% of overall binding was determined by incubation of membrane preparations with radioligand in the presence of 5 μM Serotonin (5-HT). Methiothepin was used as positive control. Binding of tested compounds with the receptor was determined by their ability to displace the radioligand and expressed in percent of displacement. The percent of displacement was calculated according to the following equation:

$$\% I = \frac{TA - CA}{TA - NA} * 100,$$

wherein: TA—was overall radioactivity in the presence of radioligand only, CA—was radioactivity in the presence of radioligand and tested compound and NA—was radioactivity in the presence of radioligand and Serotonin (5 μM).

Table 4 presents the test results for some serotonin 5-HT$_6$ receptor antagonists of general formulas 1 and 2 in the setting of competitive binding to serotonin 5-HT$_6$ receptors, testifying their high activity towards serotonin 5-HT$_6$ receptors.

TABLE 4

IC$_{50}$ values of serotonin 5-HT$_6$ receptor inhibition by antagonists of general formulas 1 and 2 in the setting of competitive binding.

| Antagonists of general formulas 1 and 2 | IC$_{50}$, nM | K$_i$, nM |
|---|---|---|
| 1.1(1) | 0.157 | 0.073 |
| 1.1(3) | 0.436 | 0.202 |
| 1.2(1) | 0.241 | 0.112 |
| 1.2(3) | 1.05 | 0.49 |
| 2(1) | 1.07 | 0.499 |
| 2(2) | 0.551 | 0.256 |

The data presented in Tables 3 and 4 give evidence that compounds of general formulas 1 and 2 could be used as "Molecular tools" for investigation of peculiarities of physiologically active compounds possessing property to inhibit serotonin 5-HT$_6$ receptors, and as drug substances for pharmaceutical compositions and medicaments.

Example 4

Preparation of medicament in the form of tablets. 1600 mg Of starch, 1600 mg of ground lactose, 400 mg of talk and 1000 mg of compound 1.1(1) were mixed together and pressed into bar. The resultant bar was comminuted into granules and sifted through sieve to collect granules of 14-16 mesh. The granules thus obtained were shaped into tablets of suitable form weighing 560 mg each.

Example 5

Preparation of medicament in the form of capsules. Compound 1.1(1) and lactose powder were carefully mixed in ratio 2:1. The resultant powdery mixture was packed into gelatin capsules of suitable size by 300 mg to capsule.

Example 6

Preparation of Medicament in Form of Compositions for Intramuscular, intraperitoneal or hypodermic injections. 500 mg Of compound 1.1(1), 300 mg of chlorobutanol, 2 ml of propylene glycol, and 100 ml of injectable water were mixed together. The resultant solution was filtered and placed into 1 ml ampoules, which were sealed and sterilized in autoclave.

Example 7

Nootropic action of compounds of general formulas 1 and 2 (enhancement of memory disturbed by Scopolamine) in the test "Passive Avoidance of mice in the Shuttle Chamber". A shuttle chamber (Ugo Basile, Italy) consisted of two sections was used. The walls of one section were opaque while the other section had transparent cover. The sections were connected through a hole which could be overlapped by vertical door. The floor was made of transverse metal bars on which DC current impulses could be fed. Experiments were carried out in aged male mice of BALB/c line weighing 20-24 grams.

On the first day of testing 30 minutes before training mice were injected intraintestinally with physiological solutions of Scopolamine (0.3 mg/kg) or Scopolamine in combination with active ingredient 1.1(1). Each group consisted of at least 8 animals. Animals were placed in light section, and latent period of the first entry into dark chamber was registered. Then vertical door was closed and the animal was punished by 0.6 mA DC current for 3 seconds. After that the animal was taken back to its homecage. In 22-24 hours the same animal was placed again in light section of the shuttle chamber and latent period of its first entry into dark section, the total time of its stay in light section and the number of entries into dark section, was registered. Each monitoring lasted for 5 minutes.

Testing was carried out during the day time in isolated laboratory using white noise at level of about 70 decibel above human hearing threshold.

Scopolamine causes disturbance of training (memory loss) that results in increased latent period for the first entry into dark section, longer stay in light section, and in decreased number of entries into dark section.

The ability of active ingredient 1.1(1) to enhance memory disturbed by Scopolamine is regarded as manifestation of its nootropic properties. The data presented confirm nootropic action of active ingredient 1.1(1).

Example 8

Nootropic action of compounds of general formulas 1 and 2 (memory enhancement disturbed by MK-801) in the test "Passive Avoidance of mice in the Shuttle Chamber". The testing was carried out as in example 7. On the first day of testing 30 minutes before training the mice were injected intraintestinally with physiological solution of MK-801 (0.1 mg/kg). Concurrently, physiological solution of MK-801 in combination with active ingredient 1.1(1) was injected intraintestinally to independent groups of mice before training.

The results obtained testify the ability of active ingredient 1.1(1) to produce nootropic effect.

Example 9

Anxiolytic (tranquilizing) action of compounds of general formulas 1 and 2 in the test "Mice Behavior in the Elevated Plus Maze". The length of each arm of the maze is 30 cm, width is 5 cm, and height of walls is 15 cm. Two opposite arms are closed from both sides and end faces by transparent walls, the other two arms are lit and opened. A mouse was placed in the center of maze, and for the next five minutes the number of entries into opened and closed arms and the time spent in each type of arms was registered. These data were used to calculate the preference indexes for opened arms as ratio of the number of opened arm entries, as well as the total time spent there to the whole number of entries to all arms and the total time spent there. The animals usually avoid opened arms (the preference index is between 0.2 and 0.3). Compounds with tranquilizing action increase this index up to 0.5-0.6 or even more and reduce the number of defecations without changing the overall motion activity of the mice (the total number of entries to the arms).

The results obtained testify that active ingredient 1.1(1) exhibits anxiolytic (tranquilizing) action which is comparable with the activity of Buspirone and Lorasepam.

INDUSTRIAL APPLICABILITY

The invention could be use in medicine, veterinary, biochemistry.

The invention claimed is:

1. A 2-alkylamino-3-(arylsulfonyl)-cycloalkyl[e]pyrazolo[1,5-a]pyrimidine compound of formula 1 or 2,

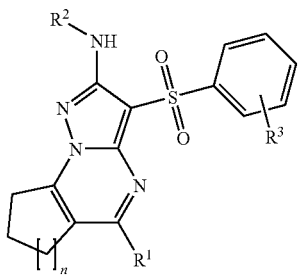

1

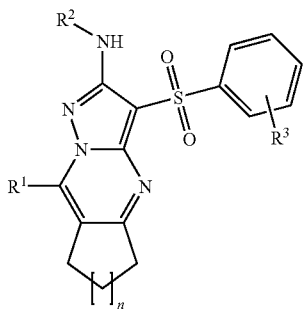

2 wherein:

$R^1$ is hydrogen or $C_1$-$C_3$ alkyl;

$R^2$ is $C_1$-$C_3$ alkyl;

$R^3$ is hydrogen, one or two optionally identical halogen, $C_1$-$C_3$ alkyl or hydroxyl group optionally substituted with $C_1$-$C_3$ alkyl;

n is integer 1, 2 or 3.

2. The compound of claim 1, selected from the group, consisting of 2-alkylamino-3-arylsulfonyl-7,8-dihydro-6H-cyclopenta[e]pyrazolo[1,5-a]pyrimidines of formula 1.1, 1.2, and 1.3,

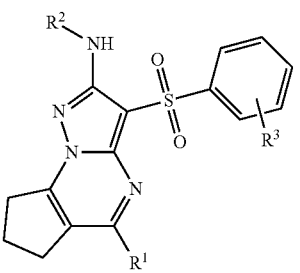

1.1

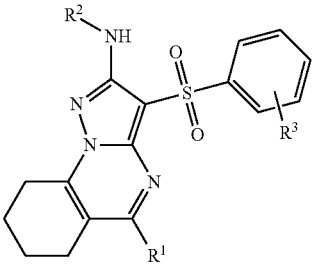

1.2

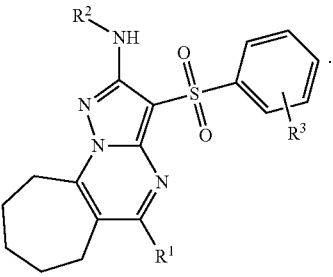

1.3

3. The compound of claim 2, selected from the group, consisting of: 2-methylamino-3-(phenylsulfonyl)-7,8-dihydro-6H-cyclopenta [e]pyrazolo[1,5-a]pyrimidine 1.1(1), 2-methylamino-3-(3-chlorophenylsulfonyl)-7,8-dihydro-6H-cyclopenta[e]pyrazolo[1,5-a]pyrimidine 1.1(2), 5-methyl-2-methylamino-3-(phenylsulfonyl)-7,8-dihydro-6H-cyclopenta[e]pyrazolo[1,5-a]pyrimidine 1.1(3), 5-methyl-2-methylamino-3-(3-chlorophenylsulfonyl)-7,8-dihydro-6H-cyclopenta[e]pyrazolo[1,5-a]pyrimidine 1.1(4), 2-methylamino-3-(phenylsulfonyl)-6,7,8,9-tetrahydrocyclohexa[e]pyrazolo[1,5-a]pyrimidine 1.2(1), 2-methylamino-3-chlorophenylsulfonyl)-6,7,8,9-tetrahydrocyclohexa[e]pyrazolo[1,5-a]pyrimidine 1.2(2), 5-methyl-2-methylamino-3-(phenylsulfonyl)-6,7,8,9-tetrahydrocyclohexa[e]pyrazolo[1,5-a]pyrimidine 1.2(3), 5-methyl-2-methylamino-3-(3-fluorophenylsulfonyl)-6,7,8,9-tetrahydrocyclohexa[e]pyrazolo[1,5-a]pyrimidine 1.2(4), 5-methyl-2-methylamino-3-(3-chlorophenylsulfonyl)-6,7,8,9-tetrahydrocyclohexa[e]pyrazolo[1,5-a]pyrimidine 1.2(5), 5-methyl-2-methylamino-3-(3-chloro-4-fluorophenylsulfonyl)-6,7,8,9-tetrahydrocyclohexa[e]pyrazolo[1,5-a]pyrimidine 1.2(6), 2-methylamino-3-(phenylsulfonyl)-7,8,9,10-tetrahydro-6H-cyclohepta[e]pyrazolo[1,5-a]pyrimidine 1.3(1), and 2-methylamino-3-(3-chlorophenylsulfonyl)-7,8,9,10-tetrahydro-6H-cyclohepta[e]pyrazolo[1,5-a]pyrimidine 1.3(2), or a pharmaceutically acceptable salt thereof,

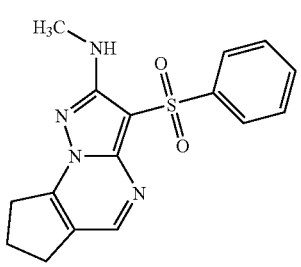

1.1(1)

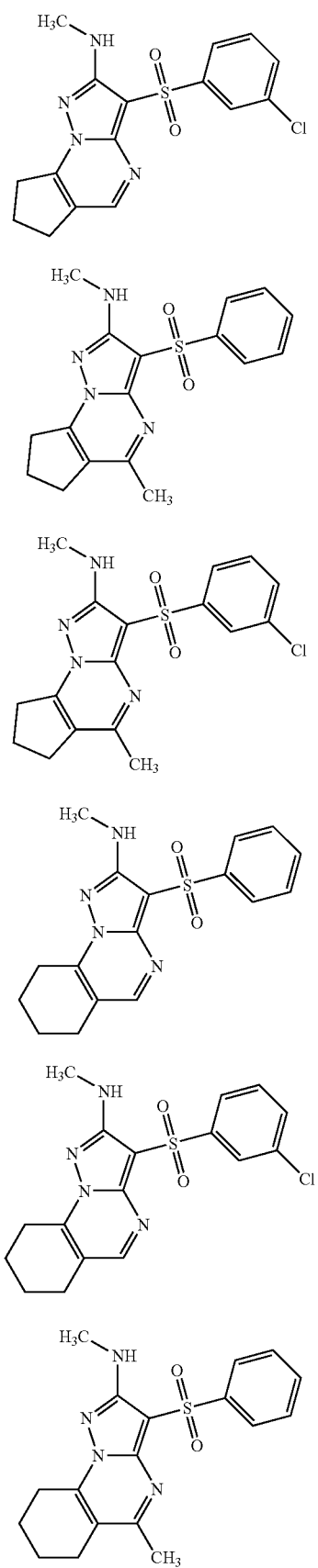
1.1(2)
1.1(3)
1.1(4)
1.2(1)
1.2(2)
1.2(3)
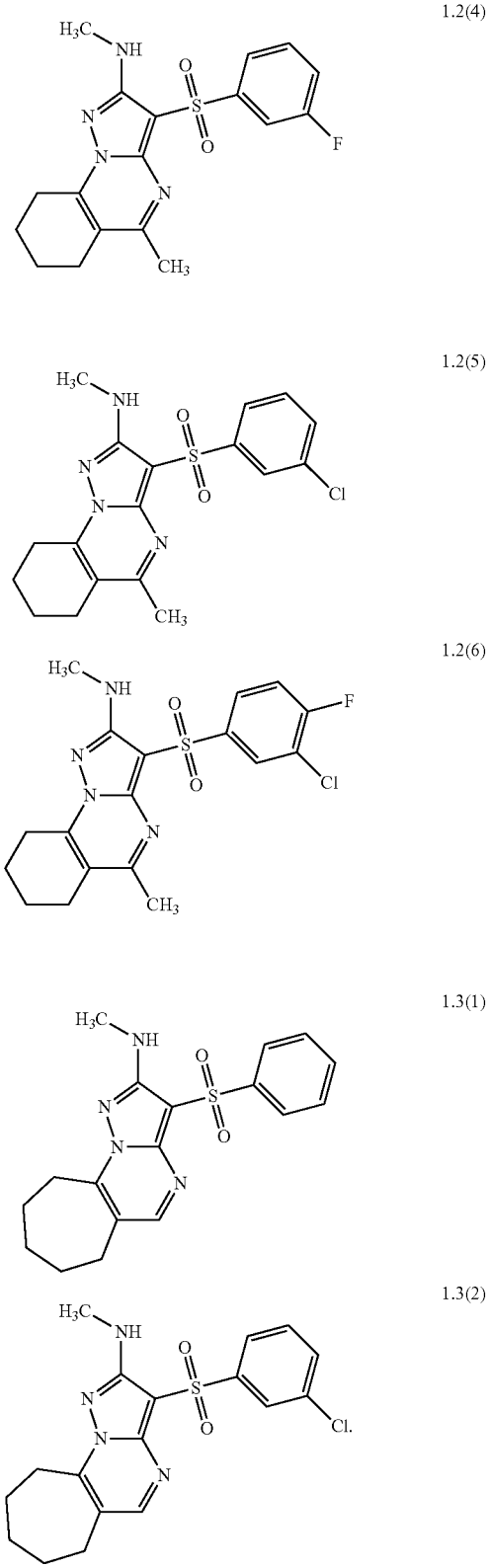
1.2(4)
1.2(5)
1.2(6)
1.3(1)
1.3(2)
4. A method for the preparation of compounds in any of claims 1-3 by mixing a compound of formula 3 with a compound of formula 4 or 5 and subsequently isolating or separating the reaction products,

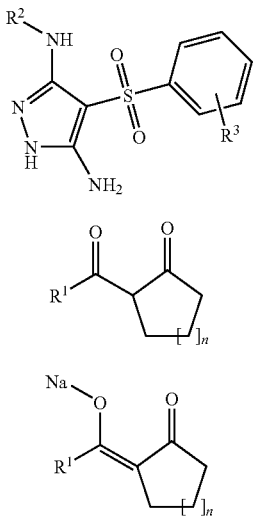

wherein: $R^1$, $R^2$ and $R^3$ are as defined in claim 1.

5. A molecular tool for investigation of peculiarities of physiologically active compounds possessing property to inhibit serotonin 5-$HT_6$ receptors comprising a compound of formula 1 or 2 according to claim 1.

6. A pharmaceutical composition comprising a pharmaceutically effective amount of a compound of formula 1 or 2 according to claim 1 and pharmaceutically acceptable carriers, including inert excipients and/or solvents.

7. A method for the preparation of pharmaceutical composition as claimed in claim 6 by mixing a compound of formula 1 or 2 according to claim 1 with inert fillers and/or diluents.

8. The pharmaceutical composition of claim 6 in the form of tablet, capsule, or injection placed in a pharmaceutically acceptable packing.

9. A therapeutic kit comprising a pharmaceutically effective amount of a compound of formula 1 or 2 according to claim 1 and active ingredient for overweight lowering and obesity treatment selected from the group consisting of anorectic drug, hormone drug, statin, hypoglycemic drug, inhibitor of ferments of fatty acids synthesis, and an antioxidant.

10. A method for treating obesity, pathogenesis of which is associated with serotonin 5-$HT_6$ receptors in human or animal, comprising administering an effective dose of a compound of claim 1 to human or animal.

* * * * *